May 29, 1962 R. V. LINDQUIST Plant Pat. 2,151
ROSE PLANT
Filed July 25, 1961
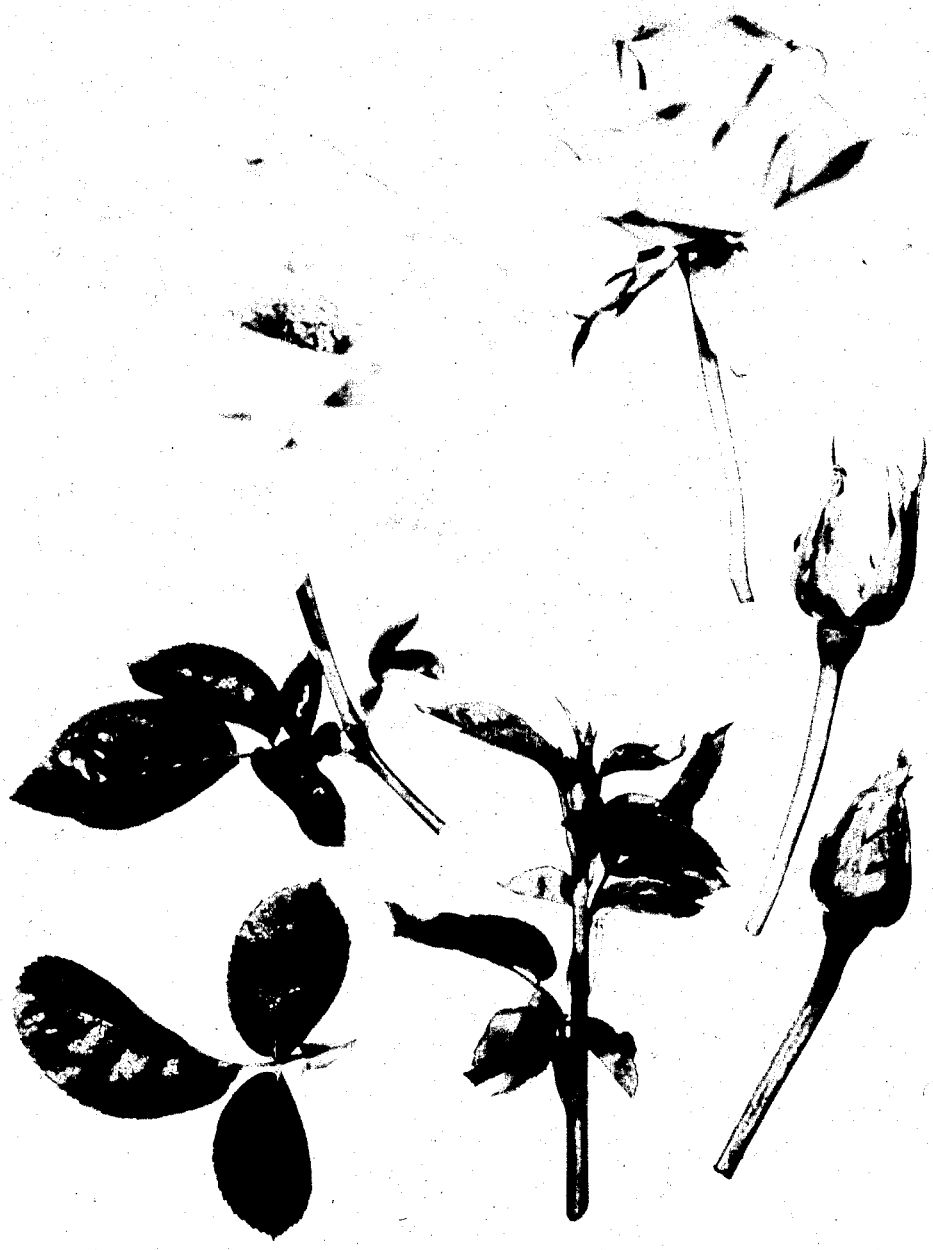
INVENTOR
Robert V. Lindquist
BY Robb & Robb
ATTORNEYS United States Patent Office Plant Pat. 2,151
Patented May 29, 1962

2,151
ROSE PLANT

Robert V. Lindquist, Hemet, Calif., assignor to Hemet Wholesale, Hemet, Calif., a partnership Filed July 25, 1961, Ser. No. 126,726
1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Duquesa de Penaranda" (unpatented).

As the result of this breeding, I have produced a new rose variety which is particularly characterized as to novelty by the following unique combination of characteristics which are outstanding in the new variety and which distinguish it from its parents, as well as from all other varieties of which I am aware:

(1) Unusual perfection of both bud and flower form;

(2) Almost complete absence of thorns on new growth producing flowers; and (3) A unique and attractive general color tonality of the flowers corresponding to near Salmon color with some shadings of near Carmine Rose on the outside petals in the case of the newly opened flowers, with the Salmon color changing to near Warm Buff as the flowers age.

Asexual reproduction of my new variety by budding, as performed at Hemet, California, shows that the foregoing characteristics and distinctions come true to form and are established and transmitted through succeeding propagations.

The accompanying drawings shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"), as indicated:

Type: Half-hardy; tall; bush; outdoor; seedling; for cut flowers and garden decoration.

Class: Hybrid tea.

Breeding: Seedling.

*Seed parent.*—"Charlotte Armstrong."

*Pollen parent.*—"Duquesa de Penaranda."

Propagation: Holds its distinguishing characteristics through succeeding propagations by budding.

*Flower*

Locality where grown and observed: Hemet, California.

Flowers borne: Usually singly, but sometimes 2 or more to stem; on strong stems ranging from medium length to long.

Quantity of bloom: Free, outdoors.

Continuity: Continuous during growing season.

Fragrance: Slight. Nature—tea.

Bud:

*Peduncle.*—Average length; from slender to average caliper; from slightly bending to erect; with some gland-tipped cilia and few prickles. Color—near Biscay Green, Plate XVII (Ridgway), with shadings of near Corinthian Purple, Plate XXXVIII (Ridgway).

*Before calyx breaks.*—Size—medium. Form—medium length; ovoid; with foliaceous appendages on the surface of the bud; usually with slender foliaceous parts extending beyond the tip of the bud equal to about ¼ of its length.

*As calyx breaks.*—Color—near Coral Red, Plate XIII (Ridgway), shading to near Coral Pink, Plate XIII (Ridgway).

*Sepals.*—Inner surface—with wooly tomentum. Margins—with few foliaceous appendages and few hairs.

*As first petal opens.*—Size—average. Form—medium length; from pointed to ovoid. Color: outside—near Flesh Ocher, Plate XIV (Ridgway), with shadings of near Salmon color, Plate XIV (Ridgway), and shading to near Empire Yellow, Plate IV (Ridgway) at base of petal; inside—near Flesh Ocher, Plate XIV (Ridgway), with shadings of near Salmon color, Plate XIV (Ridgway), and shading to near Empire Yellow, Plate IV (Ridgway) at base of petal.

*Opening.*—Opens up well.

Bloom:

*Size (when fully open).*—Average from 4 inches to 5 inches.

*Petalage.*—Double; from 25 to 30 petals, plus 4 to 6 petaloids; arranged irregularly.

*Form.*—Open and somewhat cupped at first, but becoming from flat to open; petals being at first somewhat rolled outward, but later becoming somewhat loosely rolled outward at maturity.

Petals:

*Texture.*—Medium thickness; moderately soft. Inside—slightly satiny. Outside—satiny.

*Shape.*—Outside—round, with apex rounded and with 1 or 2 notches. Intermediate—round, with apex rounded and with 1 or 2 notches. Inside—nearly oval; with apex rounded, and with 1 or 2 notches.

This description of a newly opened flower was made from a rose grown outdoors during the month of October at Hemet, California:

*Color.*—Outer petal: outside surface—near Salmon color, Plate XIV (Ridgway), shading to near Carmine Rose, Plate 621/2, page 75 (Wilson), with base near Empire Yellow, Plate IV (Ridgway); inside surface—near Salmon color, Plate XIV (Ridgway), shading to near Carmine Rose, Plate 621/2, page 75 (Wilson), with base near Empire Yellow, Plate IV (Ridgway). Intermediate petal: outside surface—near Salmon color, Plate XIV (Ridgway), shading to near Carmine Rose, Plate 621/2, page 75 (Wilson), with base near Empire Yellow, Plate IV (Ridgway); inside surface—near Salmon color, Plate XIV (Ridgway), shading to near Carmine Rose, Plate 621/2, page 75 (Wilson), with base near Empire Yellow, Plate IV (Ridgway). Inner petal: outside surface—near Salmon color, Plate XIV (Ridgway), shading to near Carmine Rose, Plate 621/2, page 75 (Wilson), with base near Empire Yellow, Plate IV (Ridgway); inside surface—near Salmon color, Plate XIV (Ridgway), shading to near Carmine Rose, Plate 621/2, page 75 (Wilson) at outside edge of petals, and with base near Empire Yellow, Plate IV (Ridgway).

This description was made from a rose that was open for three days outdoors during the month of October at Hemet, California:

*Color.*—Outer petal: outside surface—near Carmine Rose, Plate 621/3, page 75 (Wilson), with shadings of near Salmon color, Plate XIV (Ridgway), and with base near Empire Yellow, Plate IV (Ridgway); inside surface—near Carmine Rose, Plate 621/3, page 75 (Wilson), with shadings of near Salmon color, Plate XIV (Ridgway), and with base near Empire Yellow, Plate IV (Ridgway). Inner petal: outside surface—near Pale Salmon color, Plate XIV (Ridgway), with shadings of near Carmine Rose, Plate 621/3, page 75 (Wilson), and with base near Empire Yellow, Plate IV (Ridgway); inside surface—near Warm Buff, Plate XV (Ridgway), shading to near Light Buff, Plate XV (Ridgway), and with base near Empire Yellow, Plate IV (Ridgway).

*General color effect.*—Newly opened flower—near Salmon color, Plate XIV (Ridgway), with some shadings of near Carmine Rose, Plate 621/2, page 75 (Wilson) on outside petals. 3-days open—near Warm Buff, Plate XV (Ridgway), with shadings of near Carmine Rose, Plate 621/3, page 75 (Wilson).

*Behavior.*—Drop off cleanly.

*Flower longevity.*—On bush in garden—2 or 3 days in September. Cut roses grown outdoors and kept at livingroom temperatures—3 or 4 days in September.

*Reproductive Organs*

Stamens: Average number; arranged regularly about pistils.

Filaments: Medium length; most with anthers.

Anthers: Medium size; all open approximately at once. Color: upper side—Yellow Ochre, Plate 07/1, page 101 (Wilson); under side—Maize Yellow, Plate 607, page 69 (Wilson).

Pollen: Moderate quantity. Color—near Antimony Yellow, Plate XV (Ridgway).

Pistils: Average number; approximately 80 in number.

Styles: Moderately uneven; average length; average caliper; somewhat bunched.

Stigma: Color—Maize Yellow, Plate 607, page 69 (Wilson).

Ovaries: Usually all enclosed in calyx.

Hips: Average length; with inconspicuous neck; pear-shaped; smooth; thick walls. Color—near Light Orange Yellow, Plate III (Ridgway), with shadings of near Deep Chrome, Plate III (Ridgway).

Sepals: Falling soon; medium length; spear-shaped. Color: inside—near Clear Fluorite Green, Plate XXXII (Ridgway); outside—near Light Bice Green, Plate XVII (Ridgway).

Seeds: Average number (from 10 to 35); from medium size to large.

*Plant*

Foliage:

*Leaves.*—Compound of usually 5 to 7 leaflets; abundant; medium size; heavy; somewhat leathery; semi-glossy.

*Color.*—Mature: upper surface—near Elm Green, Plate XVII (Ridgway); under surface—near Light Bice Green, Plate XVII (Ridgway). Young: upper surface—near Elm Green, Plate XVII (Ridgway); under surface—near Light Bice Green, Plate XVII (Ridgway), with shadings of near Corinthian Purple, Plate XXXVIII (Ridgway).

*Rachis (the supporting stem of the compound leaf).*—Average size. Upper side—grooved; with few hairs and some stipitate glands on edges; prickly; glandular. Under side—smooth.

*Stipules.*—Medium length; medium width; with short to medium length points turning out at an angle of about 45°.

*Disease resistance.*—Mildly subject to mildew, as determined by comparison with other varieties grown under comparable cultural conditions at Hemet, California.

Growth:

*Habit.*—Upright.

*Growth.*—Moderately vigorous.

*Canes.*—Moderately heavy.

*Main stems.*—Color—near Hellebore Green, Plate XVII (Ridgway). Large prickles—very few; hooked slightly downward; with narrow base of medium length; color—near Russet, Plate XV (Ridgway). Small prickles—very few; color—near Cinnamon, Plate XXIX (Ridgway). Hairs—none.

*Branches.*—Color—near Cress Green, Plate XXXI (Ridgway). Large prickles—very few; medium length; hooked slightly downward; color—near Cinnamon Brown, Plate XV (Ridgway). Small prickles — very few; color — near Cinnamon Brown, Plate XV (Ridgway). Hairs—none.

*New shoots.*—Color—near Corinthian Purple, Plate XXXVIII (Ridgway), with shadings of near Biscay Green, Plate XVII (Ridgway). Large prickles—none. Small prickles—none. Hairs—none.

I claim:

A new and distinct variety of rose plant of the hybrid tea class, substantially as herein shown and described, characterized particularly as to novelty by the unique combination of unusual perfection of both bud and flower form, almost complete absence of thorns on new growth producing flowers, and a distinctive and attractive general color tonality of the flowers corresponding to near Salmon color with shadings of near Carmine Rose on the outside petals, changing to near Warm Buff with shadings of near Carmine Rose as the flowers age.

No references cited.